United States Patent [19]

Deberitz et al.

[11] Patent Number: 4,982,017
[45] Date of Patent: Jan. 1, 1991

[54] COMPOSITION FOR USE IN ORGANOLITHIUM SYNTHESIS REACTIONS

[75] Inventors: Jürgen Deberitz, Frankfurt; Wilfried Weiss, Oberursel, both of Fed. Rep. of Germany

[73] Assignee: Metallgesellschaft Aktiengesellschaft, Frankfurt am Main, Fed. Rep. of Germany

[21] Appl. No.: 346,868

[22] Filed: May 3, 1989

[30] Foreign Application Priority Data

May 4, 1988 [DE] Fed. Rep. of Germany ....... 3815166

[51] Int. Cl.$^5$ .................. C07C 29/09; C07C 35/08
[52] U.S. Cl. .................... 568/834; 502/152; 502/157; 568/832; 568/833; 568/835; 568/851

[58] Field of Search ............... 568/832, 833, 834, 835, 568/851; 502/157, 152

[56] References Cited

U.S. PATENT DOCUMENTS 4,370,257  1/1983  Imai et al. ........................ 568/832
4,617,145  10/1986  Schreiber et al. .................. 568/832

*Primary Examiner*—Werren B. Lone
*Attorney, Agent, or Firm*—Herbert Dubno Jonathan Myers

[57] ABSTRACT

A composition for use in synthesis reactions comprises a mixture of an organolithium compound and an inert inorganic pulverulent carrier and consists of methyllithium and ethyllithium, one or more of the group consisting of $SiO_2$, $Al_2O_3$, CaO and synthetic anhydrous aluminosilicate, and paraffin. That composition is flowable and non-pyrophoric.

8 Claims, No Drawings

COMPOSITION FOR USE IN ORGANOLITHIUM SYNTHESIS REACTIONS

FIELD OF THE INVENTION

Our present invention relates to a composition for use in synthesis reactions, comprising a mixture of an organolithium compound and an inert inorganic pulverulent carrier. The invention also relates to the reaction system containing the reaction mixture and to a reaction method.

BACKGROUND OF THE INVENTION

Organolithium compounds play an important role in preparative organic chemistry when lithium or an organic substituent is to be incorporated in an organic compound.

The organolithium compounds are usually susceptible to reaction with air and moisture and, for this reason, may be handled only with precautions. For instance, butyllithium is a self-igniting liquid, which is susceptible to hydrolysis. For this reason, butyllithium is usually handled in 15 to 25% solutions, e.g. in alkanes, or in about 30% suspensions of paraffins (Römpp Chemie Lexikon, 8th edition, 1979, page 547). By contrast with their higher homologs, methyllithium and ethyllithium are insoluble or hardly soluble in saturated and in saturated hydrocarbons and as solids are highly pyrophoric so that they can be handled only with difficulty.

From Published German application No. 36 37 780, it is known that the disadvantages of solutions of organomagnesium and organolithium compounds can be avoided by using them in pulverulent mixtures of clay dust and solutions of organomagnesium or organolithium compounds.

While the powders thus obtained are less susceptible to hydrolysis, they are pyrophoric, particularly with the organolithium compound.

In order to reduce their pyrophoric character, undesirably high clay contents are required, which in organic syntheses act as undesired accompanying substances and as sorbents.

In safety regulations for handling butyllithium, it has been stated that material which is flowing out can be treated with pulverulent limestone for preventing a fire. From "Synthesis" (1983), page 387, it is known to modify complex inorganic hydrides by incorporating them in silica gel or alumina.

The synthesis of methyllithium or ethyllithium is effected in a known manner, namely, methyllithium contained in diethyl ether or tetrahydrofuran and ethyllithium contained in hexane, by the reaction of lithium metal and alkyl halide in accordance with the formula:

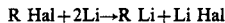

R Hal + 2Li → R Li + Li Hal

Lithiummethyl has the highest solubility in diethyl ether, in which it has a solubility of about 5%. Solutions of ethyllithium have an ethyllithium concentration of about 2%. But the restriction to diethyl ether restricts the use of that compound, because numerous users hesitate to use diethyl ether on an industrial scale owing to its high vapor pressure and the formation of peroxide upon evaporation and try to avoid such use, if possible. In addition, the solutions have only relatively low concentrations.

OBJECTS OF THE INVENTION

It is an object of the invention to provide for synthesis reactions for incorporating lithium, a composition which has a higher content of the active compound but is non-pyrophoric and is susceptible to hydrolysis and can be used in the solvents usually employed in the chemistry of the organometallic compounds and can particularly be used in hydrocarbons.

Another object is to provide an improved reaction system for a metallization or alkylation reaction whereby earlier drawbacks are avoided.

It is also an object of our invention to provide an improved reaction method.

SUMMARY OF THE INVENTION

These objects are accomplished in accordance with the invention by providing a composition for synthesis reactions which is non-pyrophoric and flowable an consists essentially of:

(a) methyllithium or ethyllithium, (b) one or more oxides of the group consisting of $SiO_2$, $Al_2O_3$, CaO and synthetic anhydrous aluminosilicate, and (c) paraffin.

Solvent-free methyllithium or ethyllithium is a self-igniting solid so that these compounds can be handled only with difficulty.

While their pyrophoric character can be suppressed by a mixing with paraffin, such as paraffin oil or paraffin waxes, a very high proportion of at least 60% will be required for that purpose. In reaction media, such as alkanes, such products consisting, e.g. of 60% solid paraffin and 40% methyllithium usually form thixotropic solutions. Mixtures with paraffin oils may become inhomogeneous by segregation caused by sedimentation.

The composition for synthesis reactions in accordance with the invention is suitably a mixture composed of:

(a) 15 to 25%, preferably 18 to 22% by weight of methyllithium or ethyllithium, (b) 35 to 45%, preferably 38 to 42% by weight oxides of the group consisting of $SiO_2$, $Al_2O_3$, CaO and synthetic anhydrous aluminosilicate, (c) 35 to 45%, preferably 38 to 42% by weight paraffin.

The method to alkylate an organic compound can comprise the steps of:

(a) forming a reaction system by suspending a mixture of:

an alkyl-lithium component consisting of at least one alkyl-lithium compound;

an inorganic component selected from the group which consists of at least one oxide selected from the group which consists of $SiO_2$, $Al_2O_3$ and CaO, and synthetic anhydrous aluminum silicate; an a paraffinic component consisting of at least one paraffin compound in an organic solvent selected from the group which consists of:

$C_5$ to $C_{10}$ saturated aliphatic hydrocarbons, $C_5$ to $C_{10}$ cycloaliphatic hydrocarbons, aromatic hydrocarbons selected from the group which consists of benzene, toluene and xylene, and aliphatic or cycloaliphatic ethers selected from the group which consists of di-isopropylether, di-n-butylether, tert.-butylether, tetrahydrofuran and dioxane;

(b) treating said organic compound with said reaction system to form an alkylated product; and (c) recovering said alkylated product from said reaction system.

For the composition for synthesis reactions in accordance with the invention, it is essential that the carrier be inert relative to the alkyllithium compound. For this reason, the content of hydroxylic groups (usually derived from hydrating water) in the oxide of the carrier should not exceed 5% by weight. Any proton activity of the carrier will be indicated by an evolution of gas. For instance, methane will be evolved when a carrier which is still proton-active, such as silicon dioxide having an atmospheric moisture content, is introduced into the solution of the methyllithium.

The alkyllithium compound which is still in the solution from its production is absorbed by the particulate inert carrier. Upon removal of the solvent, a pyophoric solid product will be obtained.

For this reason, it is a feature of the invention that the composition for use in synthesis reactions contains paraffin, which is a further component that is essential for the invention and shields the reactivity of the lithium compound from the atmosphere.

Suitable paraffins include solid, waxlike and liquid paraffins. In order to avoid an occasional occurrence of thixotropic effects in solvents, the composition for use in synthesis reactions in accordance with the invention preferably contains paraffin oil, particularly a viscous paraffin oil having a density of 0.860 to 0.892.

The composition for use in synthesis reactions in accordance with the invention permits the use of methyllithium and ethyllithium in solvents other than the diethylether and hexane, respectively, which were previously available.

Such other solvents are saturated aliphatic or cycloaliphatic $C_5$-$C_{10}$ hydrocarbons, aromatic hydrocarbons of the group consisting of benzene, toluene, xylene, aliphatic or cycloaliphatic ethers of the group consisting of di-isopropylether, di-n-butylether, tert.-butylether, tetrahydrofuran, and dioxane.

When the composition for use in synthesis reactions in accordance with the invention is used for carrying out organolithium metallizing or alkylating reactions, the paraffin oil may be washed out with hydrocarbon solvents before the synthesis if this is required.

The reactivity may be somewhat lower than in ethereal solutions but this effect can be compensated by somewhat higher temperatures and/or longer-reaction times or by an addition of Lewis bases (tetrahydrofuran, tetramethylene diamine).

Desirable results will be produced by the carrier particularly in the hydrolytic processing of the reaction mixtures. For instance, sludges which can conveniently be separated will be obtained because surplus water will be absorbed by the carrier.

The composition for use in synthesis reactions in accordance with the invention is produced by known methods for the production of methyllithium or ethyllithium in diethyl ether and hexane, respectively.

The solution of 5% methyllithium in ether or the solution of 2% ethyllithium in hexane is charged under a protective gas atmosphere and with constant stirring into a reactor, which contains a mixture of paraffin oil and an anhydrous oxide, such as $SiO_2$, $CaO$ or anhydrous synthetic aluminosilicate.

After homogenization in the liquid phase, ether is substantially removed from the mixture at 40° C. and under a reduced pressure of 700 mbars and the mixture is subsequently dried at 40° C. and 10 mbars. The dried product is granular and friable and is flowable It will be understood that equal results will be obtained when the solution of methyllithium or ethyllithium is held in the reactor under a protective gas and the anhydrous oxide and the paraffin are charged into the solution individually or jointly and with stirring.

The advantages afforded by the composition for use in synthesis reactions in accordance with the invention are seen in that a pyrophoric organometallic solid is transformed to a non-pyrophoric form by the addition of paraffin and the non-pyrophoric material is rendered flowable by the further addition of an inert solid. The composition for use in synthesis reactions which has been rendered inert and is non-pyrophoric, flowable and free of solvent is also eminently suitable for being transported and handled in organolithium syntheses.

EXAMPLES

The invention will be explained in greater detail with reference to the following Examples.

EXAMPLE 1

This control example shows that a product of methyllithium and paraffin alone does not have satisfactory properties.

12 g paraffin oil having a density of 0.865 were added under a protective gas and with stirring to 200 ml of a solution of 5% methyllithium in diethyl ether. The mixture was homogenized and subsequently the ether was removed from the mixture at 40° C. and 700 mbars and with constant stirring and was dried at 40° C. and 10 mbars with continued stirring for about 60 minutes. The resulting product was composed of 37% by weight methyllithium and 63% paraffin oil and had a friable, but sticky consistency and did not exhibit pyrophoric properties. Products which were friable and flowable were obtained from similar mixtures which contained solid paraffin waxes but their use in organolithium syntheses involved difficulties in processing because thixotropic solutions formed in the reaction media.

EXAMPLE 2

For a production of a flowable, non-pyrophoric composition for use in synthesis reactions, 67.4 g $Al_2O_3$ (water content 0.5%, particle size 60 to 100 μm) and 69.7 g paraffin oil having a density of 0.865 were charged into a flashlike reactor and were mixed with stirring.

Under a protective gas and with constant stirring, 1000 ml of a solution of 5.6% methyllithium in diethyl ether were then charged. 7.3 liters of methane were evolved during the addition. The temperature rose by 4° C. from an initial value of 20° C.

Substantially all diethyl ether was removed from the resulting suspension at 40° C. and 700 mbars under a protective atmosphere and with constant stirring and the suspension was subsequently evaporated to dryness at 40° C. and 10 mbars for about 60 minutes. The product now obtained was friable, flowable and non-pyrophoric. When the white product is stored on the air, it will not ignite but will slowly lose its activity and assume a yellowish color.

An analysis of the freshly produced product indicated a total basicity of 20.42% and an active basicity of 16.70%. The "active basicity" is the content of active R-Li in the compound, as determined in accordance with Zerewitinow; and the "total basicity" is the content of active R-L plus other lithium bases (Li-OR, Li-OH) calculated as LiOH and determined by titrimetry.

EXAMPLE 3

For the production of another flowable and non-pyrophoric composition for use in synthesis reactions, 34.1 g of a synthetic anhydrous aluminosilicate having a particle size of 10 to 10 $\mu$m and 94.1 g paraffin oil having a density of 0.865 were mixed with stirring in a flashlike reactor and were then mixed and homogenized under a protective gas atmosphere with 1000 ml of a solution of 5.3% ethyllithium in diethyl ether at 20° C. The temperature rose by 1° C. and 2100 ml methane were evolved.

Substantially all diethyl ether was then removed from the resulting suspension at 40° C. and 700 mbars with stirring while the protective gas atmosphere was maintained. The suspension was subsequently evaporated to dryness with constant stirring at 40° C. and 10 mbars for about 60 minutes. The resulting product was friable, flowable and non-pyrophoric. An analysis of the freshly produced product indicated a total basicity of 22.36% and an active basicity of 20.37%.

Similar results are produced when CaO is used as a carrier in Examples 2 and 3. The contents of lithium compound and paraffin oil will depend on the particle size of the carrier and on the surface area which is available. The larger the surface area of the carrier, the higher will be the content of the lithium compound which is taken-up and the required content of paraffin oil, within the limits stated.

The average content of the lithium compound in the carrier usually amounted to about 20 to 25%.

EXAMPLE 4

In this example, the alkylation of cyclohexanone with the aid of the composition for synthesis reactions in accordance with the invention will be described.

For that purpose, a mixture having the following composition and suspended in 400 ml n-pentane was charged under a nitrogen atmosphere into a reactor provided with a dripping funnel, stirrer and reflux condenser:

22.9% methyllithium (R-Li content 340 mmol)
39.1% paraffin oil (density 0.865)
37.9% $Al_2O_3$ (water content 0.5%)

360 mmol cyclohexanone was added at a controlled rate during 100 minutes This resulted in a temperature rise to 29° C. The reaction mixture was maintained at 36° C. for a further two hours under reflux conditions. The reaction mixture was subsequently hydrolyzed by an addition of 12 g water with cooling. The properly settling precipitate was filtered off and the pentane was removed from the precipitate by distillation. 60.5 g of a crude product were obtained, in which the ratio of cyclohexanone to 1-methylcyclohexanol amounted to 9.6:90.4. 1-methylcyclohexanol was isolated by distillation.

We claim:

1. A composition for use in a synthesis reaction which consists essentially of a mixture of:
    substantially 15 to 25% by weight of methyl lithium or ethyl lithium;
    substantially 35 to 45% by weight of an inorganic compound selected from the group which consists of at least one metal oxide selected from the group which consists of $SiO_2$, $Al_2O_3$, and CaO, and synthetic anhydrous aluminum silicate; and
    substantially 35 to 45% by weight of a paraffin oil or wax.

2. The composition defined in claim 1 which consists essentially of:
    18 to 22% by weight of methyl lithium or ethyl lithium;
    38 to 42% by weight of said inorganic compound; and
    38 to 42% by weight of the paraffin oil or wax.

3. The composition defined in claim 1 wherein hydroxyl group content of said inorganic compound is no more than 5% by weight.

4. The composition defined in claim 1 wherein said paraffin oil has a density of 0.860 to 0.892.

5. A synthesis reaction system for organolithium alkylation or metallization reactions comprising:
    a solvent selected from the group which consists of $C_5$ to $C_{10}$ saturated aliphatic hydrocarbons, $C_5$ to $C_{10}$ cycloaliphatic hydrocarbons, aromatic hydrocarbons selected from the group which consists of benzene, toluene and xylene, and aliphatic or cycloaliphatic ethers selected from the group which consists of diisopropyl ether, di-n-butyl ether, tert-butylether, tetrahydrofuran and dioxane; and
    a reactant dispersed in said solvent and consisting essentially of a mixture of:
    substantially 15 to 25% by weight of methyl lithium or ethyl lithium;
    substantially 35 to 45% by weight of an inorganic compound selected from the group which consists of at least one metal oxide selected from the group which consists of $SiO_2$, $Al_2O_3$, and CaO, and synthetic anhydrous aluminum silicate; and
    substantially 35 to 45% by weight of a paraffin oil or wax.

6. The reaction system defined in claim 5 wherein said mixture consists essentially of:
    18 to 22% by weight of methyl lithium or ethyl lithium;
    38 to 42% by weight of said inorganic compound; and
    38 to 42% by weight of the paraffin oil or wax.

7. The reaction system defined in claim 6 wherein hydroxyl group content of said inorganic compound is no more than 5% by weight.

8. The reaction system defined in claim 7 wherein said paraffin oil has a density of 0.860 to 0.892.

* * * * *